United States Patent
Kurz et al.

(10) Patent No.: US 7,603,788 B2
(45) Date of Patent: Oct. 20, 2009

(54) DEVICE FOR ADJUSTING THE LENGTH OF MIDDLE EAR IMPLANTS

(75) Inventors: Heinz Kurz, Dusslingen (DE); Uwe Steinhardt, Hirrlingen (DE)

(73) Assignee: Heinz Kurz GmbH Medizintechnik, Dusslingen (DE)

( * ) Notice: Subject to any disclaimer, the term of this patent is extended or adjusted under 35 U.S.C. 154(b) by 721 days.

(21) Appl. No.: 10/579,924

(22) PCT Filed: Jun. 29, 2005

(86) PCT No.: PCT/EP2005/006972

§ 371 (c)(1),
(2), (4) Date: May 19, 2006

(87) PCT Pub. No.: WO2006/050761

PCT Pub. Date: May 18, 2006

(65) Prior Publication Data

US 2007/0150057 A1 Jun. 28, 2007

(30) Foreign Application Priority Data

Nov. 12, 2004 (DE) .................. 20 2004 017 593 U (51) Int. Cl.
- G01B 5/02 (2006.01)
- A61B 5/103 (2006.01)
- A61F 2/18 (2006.01)

(52) U.S. Cl. .................... 33/512; 33/562; 600/587; 623/10

(58) Field of Classification Search ............ 33/511, 33/512, 562; 600/25, 587; 607/57; 623/10, 623/901

See application file for complete search history.

(56) References Cited

U.S. PATENT DOCUMENTS

| 4,288,066 | A | | 9/1981 | Treace et al. | |
|---|---|---|---|---|---|
| 4,921,498 | A | * | 5/1990 | Bays et al. | 623/10 |
| 5,554,188 | A | * | 9/1996 | Prescott | 623/10 |
| 5,618,292 | A | * | 4/1997 | Poler | 33/512 |
| 6,637,121 | B2 | * | 10/2003 | Barefoot | 33/562 |
| 6,892,466 | B2 | * | 5/2005 | Kurz et al. | 33/512 |
| 2004/0181280 | A1 | * | 9/2004 | Antonelli et al. | 623/10 |
| 2006/0058875 | A1 | * | 3/2006 | Reitan et al. | 623/10 |

FOREIGN PATENT DOCUMENTS

| DE | 202 01 303 | 4/2002 |
|---|---|---|
| EP | 1 449 499 | 8/2004 |
| GB | 2 257 911 | 1/1993 |

\* cited by examiner

Primary Examiner—G. Bradley Bennett
(74) Attorney, Agent, or Firm—Michael J. Striker (57) ABSTRACT

A device for determining the required length of a middle ear prosthesis, having a disk-shaped base part to which prosthesis mockups or prostheses of different lengths are fastened, which, after being detached from the base part, can be inserted by an applicator into the middle ear of a patient during an operation for length determination purposes, in which the base part is provided with accessories for measuring and/or shaping the middle ear prosthesis to be inserted, so that this provides the operator with an even more simplified handling of prosthesis mockups or prostheses during the operation; no additional separate parts have to be used and instead, the handling means are compactly provided on or integrated into the device itself.

38 Claims, 11 Drawing Sheets

DEVICE FOR ADJUSTING THE LENGTH OF MIDDLE EAR IMPLANTS

BACKGROUND OF THE INVENTION

The invention relates to a device for determining the required length of a middle ear implant with a disk-shaped base part to which prosthesis mockups of various lengths are attached, which, after being detached from the base part, can be inserted by means of an applicator into the middle ear of a patient during an operation for length determination purposes.

A device of this kind is known from EP 1 449 499 A2.

The device serves as an accessory for adjusting the length of middle ear implants, in particular partial or total protheses, during an operation on the human ear. In this case, entirely or partially missing ossicles of the human middle ear, which are supposed to transmit the sound from the eardrum to the stapes or stapedial footplate, are replaced by means of a corresponding middle ear prosthesis to be individually adapted to the specific proportions of the particular patient. Since the dimensions and geometries are different in the ear of each person, a total reconstruction requires the distance to be precisely determined between the eardrum and the stapedial footplate and a partial reconstruction requires the distance to be precisely determined between the eardrum and the stapedial head before a corresponding prosthesis can be inserted. To this end, prosthesis mockups of various sizes, which have typically the shape and form of a normal prosthesis are inserted into the middle ear of the patient during the operation in order to make a precise length determination.

Since prosthesis mockups of this kind are naturally very small, they are quite difficult and complex to manipulate, particularly in terms of their cleaning and sterilization. This is why the device described in the above-mentioned EP 1 449 499 A2 was developed, which supplies the prosthesis mockups in an easy-to-manipulate form on the circumference of a base part, attached by means of bridge pieces. After they are detached from the base part, the mockups can be inserted into the middle ear of the patient by means of a suitable applicator for purposes of length determination.

SUMMARY OF THE INVENTION

The object of the present invention is to improve a species-defining device of the type described at the beginning so as to provide the operator with a simplified handling of prosthesis mockups during the operation; no additional separate parts should be used but instead, the handling means should be compactly provided on or integrated into the device itself.

According to present invention, this object is attained in a surprisingly simple and effective manner in that the base part is provided with accessories for measuring and/or shaping the middle ear prosthesis to be inserted. Whereas with the known device, only the mockups themselves are attached to the base part, now the operator can use the disk-shaped base part to measure and shape the middle ear prosthesis to be used, without requiring other parts and additional space for this. Since the device according to the invention must be provided in a sterile form anyway, the measuring and shaping devices on the base part are automatically sterile so that the middle ear prosthesis to be inserted and/or adapted can then be taken off and shaped with no trouble during the operation.

In a particularly preferred embodiment form of the device according to the invention, the accessories include one or more recesses provided on the top and/or bottom side of the disk-shaped base part, which have an inner diameter that corresponds to the outer diameter of a head plate of the middle ear prosthesis to be inserted. The head plate of the desired middle ear prosthesis can then be inserted into these recesses and shaped during the operation.

In an advantageous modification of this embodiment form, under each recess, a cavity is provided that extends into the base part and serves in particular to accommodate a bell, which is mounted under the head plate of the middle ear prosthesis and is used to attach the middle ear prosthesis to the stapes of the middle ear, or serves to accommodate a strut, which is mounted under the head plate of the middle ear prosthesis and is used to support the middle ear prosthesis on the stapedial footplate of the middle ear. This geometric embodiment significantly facilitates handling of the prosthesis and prevents it from slipping out of the recess in the base part since the corresponding bell or strut protrudes into the cavity underneath it.

A particularly favorable embodiment form in terms of handling is achieved when the contour of the inner diameter of the recesses partially corresponds to the outer contour of the head plate of the middle ear prosthesis but in at least one section, is widened radially outward in comparison to the maximum outer diameter of the head plate. This makes it possible for the head plate of the middle ear prosthesis inserted into the recess of the base part to be wedged into place without damaging it since this head plate can be easily detached again by means of the widening of the maximum outer diameter of the recess.

In an entirely preferred modification of the above-described embodiment form of the device according to the invention, the base part is provided with a number of recesses distributed around the circumference of the base part, which correspond to the outer diameters of the head plates of the middle ear prostheses and are each of different depths. This makes it possible to accommodate middle ear prostheses of different lengths in different recesses of the base part so that precisely the right recess on the base part can be reserved for the respectively required optimal length.

The operator can be provided with a further simplified handling of the device according to the invention if the base part is provided with a mark or label next to each recess, which correlates to the respective depth of the corresponding recess and length of the head plate that can be accommodated therein and/or to the size of the inner diameter of the corresponding recess and outer diameter of the head plate and/or to the shape of the recess and head plate. It is thus possible for the operator to select at a glance the correct recess for the desired size of the middle ear prosthesis to be inserted.

Another preferred embodiment form of the device according to the invention is distinguished by the fact that the accessories include at least one conical protrusion with a preferably rounded tip that protrudes from one side of the base part and is used to widen the inner diameter of a bell, which is mounted under the head plate of the middle ear prosthesis and is used to attach the middle ear prosthesis to the stapes of the middle ear. In the event that the bell of the partial prosthesis does not precisely fit onto the stapes of the middle ear, this allows it to be precisely adapted to the actual geometric conditions in the ear of the patient, without the operator having to resort to using an additional sterile device.

In this connection, one advantageous modification is comprised of a combination of the above-described embodiment forms in which the conical protrusion is situated on the same side of the disk-shaped base part as the recess(es) for accommodating the head plate of a middle ear prosthesis. This significantly facilitates handling because the prosthesis that has been preshaped in the recesses can have be shaped further on the same side of the disk-shaped base part, without the base part having to be turned over. In particular, the conical protrusion can be situated in a cavity on this side of the disk-shaped base part, close to the recesses for accommodating the head plate.

Another particularly preferred embodiment form of the device according to the invention is distinguished by the fact that the accessories include at least one, preferably several hollows in the base part, which are designed for accommodating and possibly measuring and/or shaping a cartilage or fascia disk that serves as an insert between the middle ear prosthesis and the eardrum in order to mechanically protect the latter. Hollows of this kind for shaping cartilage or fascia disks are also referred to as "templates", but are usually contained in other devices provided expressly for this purpose, which in turn must be sterilized for the operation and would take up additional space while the device according to the invention permits this shaping to be carried out compactly on the disk-shaped base part.

Preferably, the hollows for accommodating cartilage or fascia disks have a round or oval contour. This corresponds to the usual shape of these disks in relevant operations. Since the geometric proportions, as mentioned above, are different in every patient, it is advantageous if in the device according to the invention, the base part is provided with a number of hollows of differently sized inner diameters and/or different depths so that the cartilage or fascia disks required in the individual case can be prepared using the existing device, without the use of additional devices.

In another preferred embodiment form of the device according to the invention, the accessories include at least one essentially flat preparation area on at least one side of the disk-shaped base part. In this preparation area, additional work steps can be performed on the middle ear prosthesis to be inserted and/or on possibly prepared cartilage or fascia disks. In this connection, it is extremely helpful to the operator if in modifications of this embodiment form, at least one location of the preparation area is provided with a length scale on the surface of the base part, preferably calibrated in millimeters. This makes it possible at a glance to perform absolute size comparisons or measurements, without additional accessories.

In a particularly preferred combination of the above-described embodiment forms, the hollows for accommodating cartilage or fascia disks are provided in the preparation area. This permits a "seamless" transition between the individual preparation steps in the same narrow spatial region.

An advantageous and particularly simple handling is also achieved in a modification of the invention in which the recesses for accommodating the head plate of a middle ear prosthesis on the one hand and the preparation area and possibly one or more hollows for accommodating cartilage or fascia disks on the other hand are situated on two different, preferably opposing, sides of the disk-shaped base part.

In a very particularly preferred embodiment form of the device according to the invention, as is already known from the EP 1 449 499 A2 cited at the beginning, in which the prosthesis mockups are attached to bridge pieces and distributed like satellites around the outer circumference of the disk-shaped base part. As a rule, they are attached by means of easily breakable plastic bridge pieces, which permit the operator to remove a prosthesis mockup of the desired size from the base part with no trouble and to insert it into the middle ear of the patient for measurement purposes.

In order to protect the relatively small and delicate prosthesis mockups from mechanical damage during transport, in a modification of this embodiment form, protective projections, in particular rod-shaped ones, situated between each pair of prosthesis mockups are distributed over the circumference of the disk-shaped base part and protrude beyond the prosthesis mockups in the radial direction.

A particularly advantageous geometrical embodiment of the device according to the invention is distinguished by the fact that the disk-shaped base part has a polygonal, in particular hexagonal or octagonal, outer circumference and the protective projections protrude outward in the radial direction from the vertices of the base part.

In order to save the operator unnecessary movements, in the device according to the invention, the prosthesis mockups attached to the base part should be of different sizes, in particular different lengths. The work of the operator can be further facilitated in modifications of the above-mentioned embodiment form of the invention in which the prosthesis mockups are situated on the outer circumference of the base part, each in the radial vicinity of a recess for accommodating the head plate of a middle ear prosthesis and in which the size of the recess corresponds to the size of the prosthesis mockup respectively adjacent to it. This permits a rapid visual association without requiring measurements to be carried out first.

The device according to the invention can be manufactured in a particularly inexpensive manner and in large production runs if the base part, the bridge pieces, and the prosthesis mockups are injection molded out of plastic and are preferably integrally joined to one another.

Other defining characteristics and advantages of the invention ensue from the claims and from the following detailed description of exemplary embodiments of the invention in conjunction with the drawings, which show details essential to the invention. The individual defining characteristics can be provided individually or can be united into arbitrary combinations in variants of the invention.

BRIEF DESCRIPTION OF THE DRAWINGS

The schematic drawings show exemplary embodiments of the invention that will be explained in greater detail in the description that follows.

FIG. 5b shows the shaping of a middle ear prosthesis inserted into the recess by means of microforceps;

DESCRIPTION OF THE PREFERRED EMBODIMENTS

The device according to the invention for determining the required length of a middle ear prosthesis includes a disk-shaped base part 10, 20, 30 as is shown in all of the figures in the drawings. As a rule, this disk-shaped base part is embodied in the form of a plastic injection molded component equipped with easily detachable prosthesis mockups 11, 11', 11"; 21, 21', 21"; 31, 31', 31" fastened to bridge pieces mounted along its circumference. These prosthesis mockups, after being detached from the base part 10, 20, 30, can be inserted by means of an applicator into the middle ear of a patient during an operation for length determination purposes.

Figure 1:
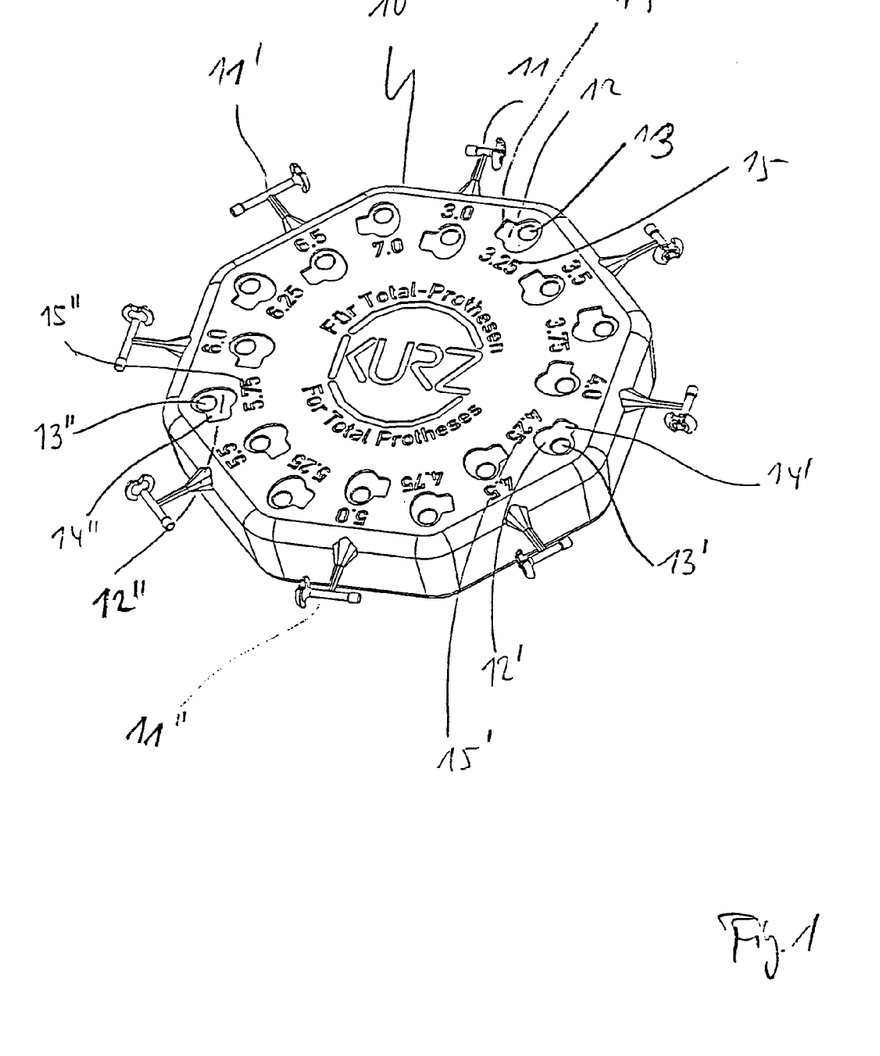
FIG. 1 shows an embodiment form of the device according to the invention, with prosthesis mockups of total prostheses for the middle ear, schematically depicted obliquely from above, looking toward the side of the base part in which the recesses and cavities are provided for accommodating the head plate of the middle ear prostheses.

According to the invention, the base part 10, 20, 30 is supplied with accessories for measuring and/or shaping middle ear prostheses to be inserted. In the embodiment form shown in FIG. 1, these accessories include a number of recesses 12, 12', 12" provided on the top side of the disk-shaped base part 10, which have an inner diameter that corresponds to the outer diameter of a head plate of the middle ear prosthesis to be inserted. Under each of these recesses 12, 12', 12", a cavity 13, 13', 13" extending into the base part 10 is provided, which, in the case of the embodiment form according to FIG. 1, serves to accommodate a strut that is mounted under the head plate of the middle ear prosthesis and is used to support the middle ear prosthesis against the stapedial footplate of the middle ear. The contour of the inner diameter of the recesses 12, 12', 12" is widened radially outward in comparison to the maximum outer diameter of the head plate in a segment 14, 14', 14" so that this head plate can be easily removed again, even if it gets wedged in place. Next to the recess 12, 12', 12", a label 15, 15', 15" is provided, which, in the present exemplary embodiment, informs the operator as to the depth of the associated cavity 13, 13', 13".

Figure 2:
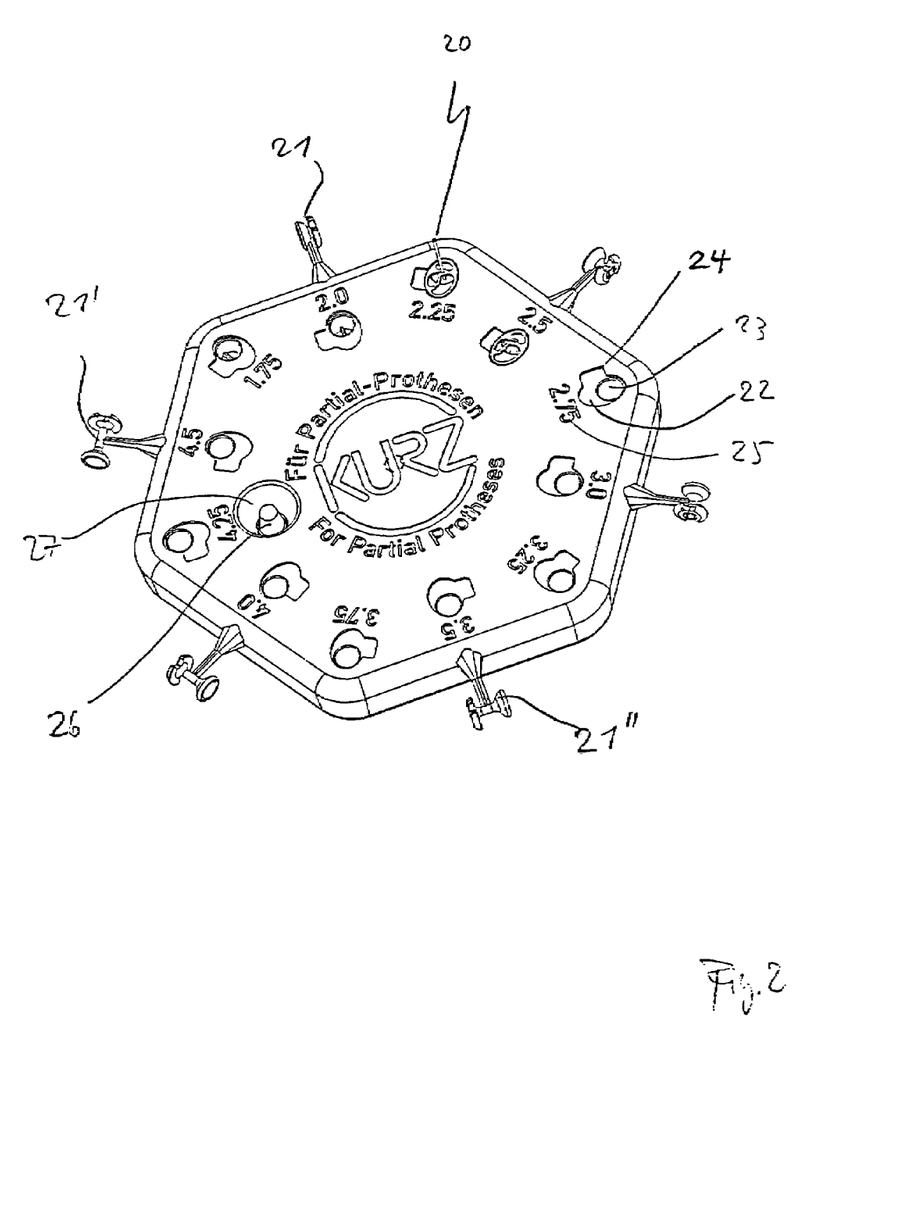
FIG. 2 shows a view similar to FIG. 1, but in an embodiment form with prosthesis mockups of partial prostheses for the middle ear and a cone for shaping the bell.
Figure 3:
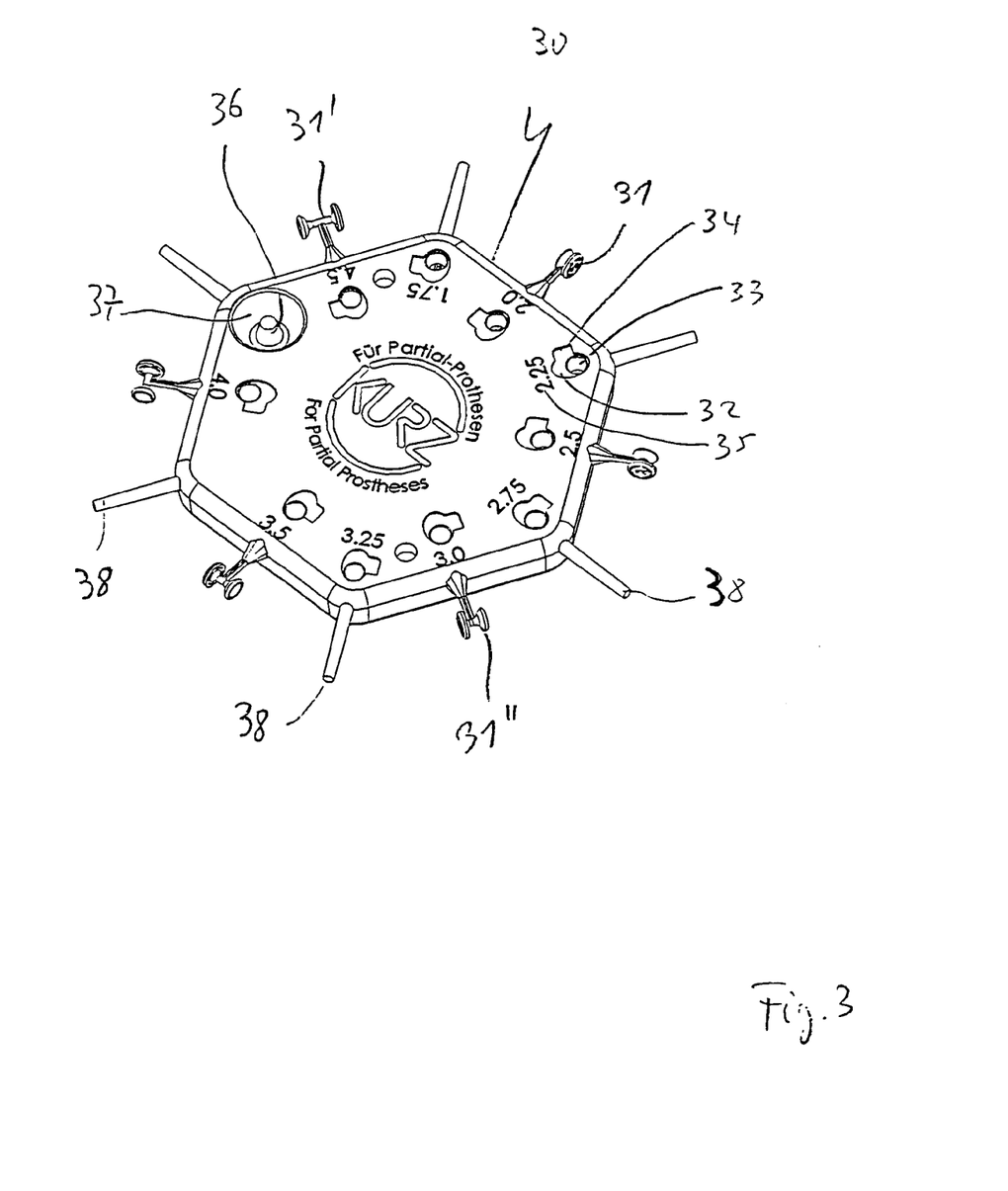
FIG. 3 shows an embodiment form similar to FIG. 2, but with additional protective projections at the vertices of the disk-shaped base part.

Similar recesses 22; 32 with associated cavities 23; 33, segments 24; 34 that are widened radially outward, and labels 25; 35 are also provided in the embodiment forms according to FIGS. 2 and 3, which are suitable for shaping partial prostheses for the middle ear. The corresponding prosthesis mockups 21, 21', 21"; 31, 31', 31" are therefore correspondingly shorter than the prosthesis mockups 11, 11', 11" shown in FIG. 1.

In order to shape bells usually provided on partial prostheses for the middle ear, particularly in order to widen them to suit individual circumstances, the embodiment forms according to FIGS. 2 and 3 have conical protrusions 26; 36 with rounded tips, each provided in a hollow 27; 37 situated on the same side of the disk-shaped base part 20; 30 as the above-described recesses 22; 32.

In addition to the embodiment form according to FIG. 2, the device according to FIG. 3 is provided with protective projections 38 at the vertices of the base part 30, protruding radially outward beyond the prosthesis mockups 31, 31', 31", thus mechanically protecting the prosthesis mockups 31, 31', 31" during transport of the device.

Figure 4:
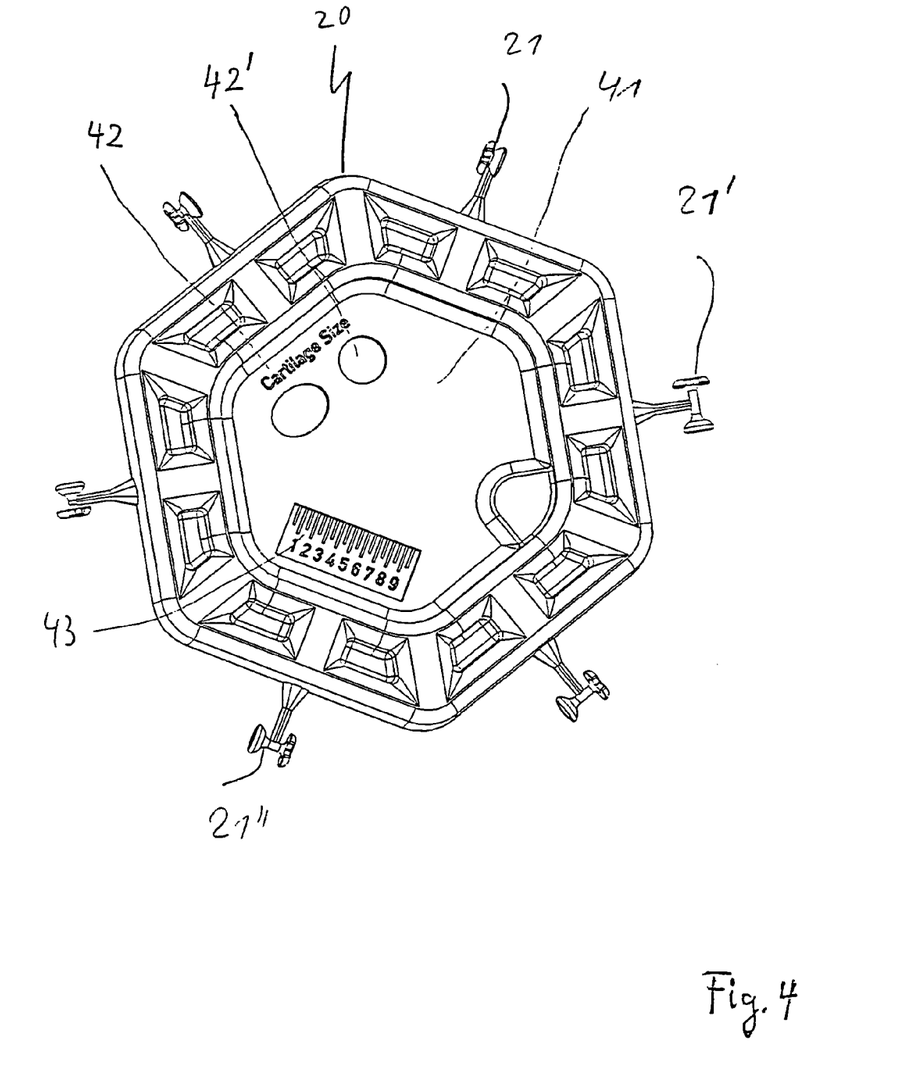
FIG. 4 shows the embodiment form similar to FIG. 2 from the rear side of the base part, showing the preparation area for cartilage or fascia disks.

FIG. 4 shows the device in FIG. 2 from below. Here, an essentially flat preparation area 41 is visible, the edge of which is provided with different sizes of oval or round hollows 42, 42' for accommodating cartilage or fascia disks that serve as inserts between the middle ear prosthesis and the eardrum in order to mechanically protect the latter. The edge of the preparation area is also provided with a length scale 43, which can preferably be calibrated in millimeters and shows the operator at a glance the absolute sizes of the parts or transplants to be shaped.

Figure 5A:
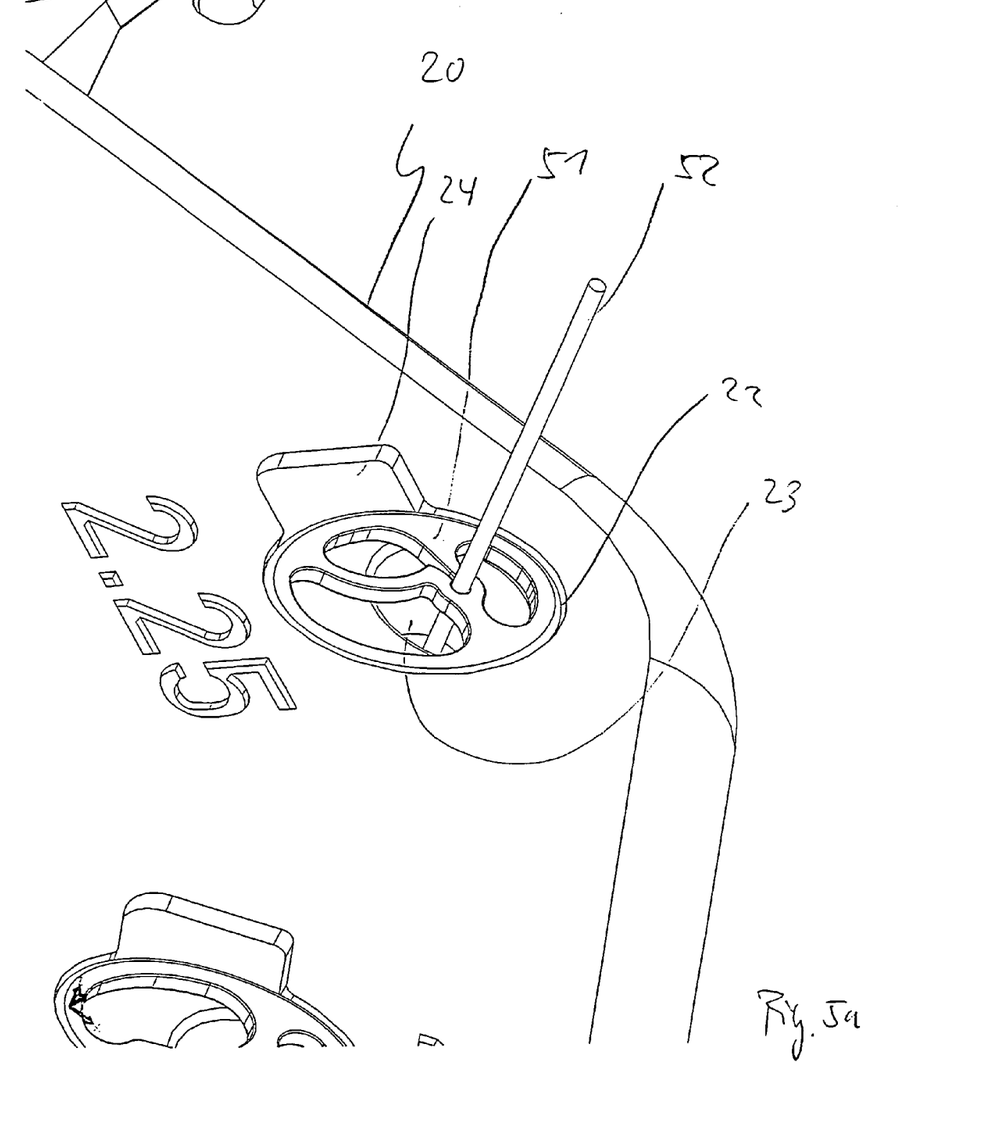
FIG. 5a is a schematic, detailed view of a recess for accommodating the head plate of a middle ear prosthesis.

FIGS. 5a through 5d depict the shaping of middle ear prostheses in one of the recesses 22 of a base part 20 (as shown in FIG. 2). FIG. 5a shows a head plate 51 with a shaft 52 that is inserted into a geometrically fitting recess 22. The other end of the shaft 52 protrudes into the cavity 23 provided underneath the recess 22 in the base part 20. In order to remove the middle ear prosthesis from the recess 22, the head plate 51 can be easily grasped by means of the radially bulging section 24 and then pushed out.

The section 24 serves as a spatial widening for the closing of the head plate as shown in FIG. 5b. The removal of the prosthesis is executed by means of tweezers on the shaft or the plastic piece is rotated.

In FIG. 5b, a microforceps 61 is used to straighten a bridge piece of the head plate so that the distance closes and the head plate is affixed to the shaft 52 of the prosthesis in a frictionally engaging fashion.

Figure 5C:
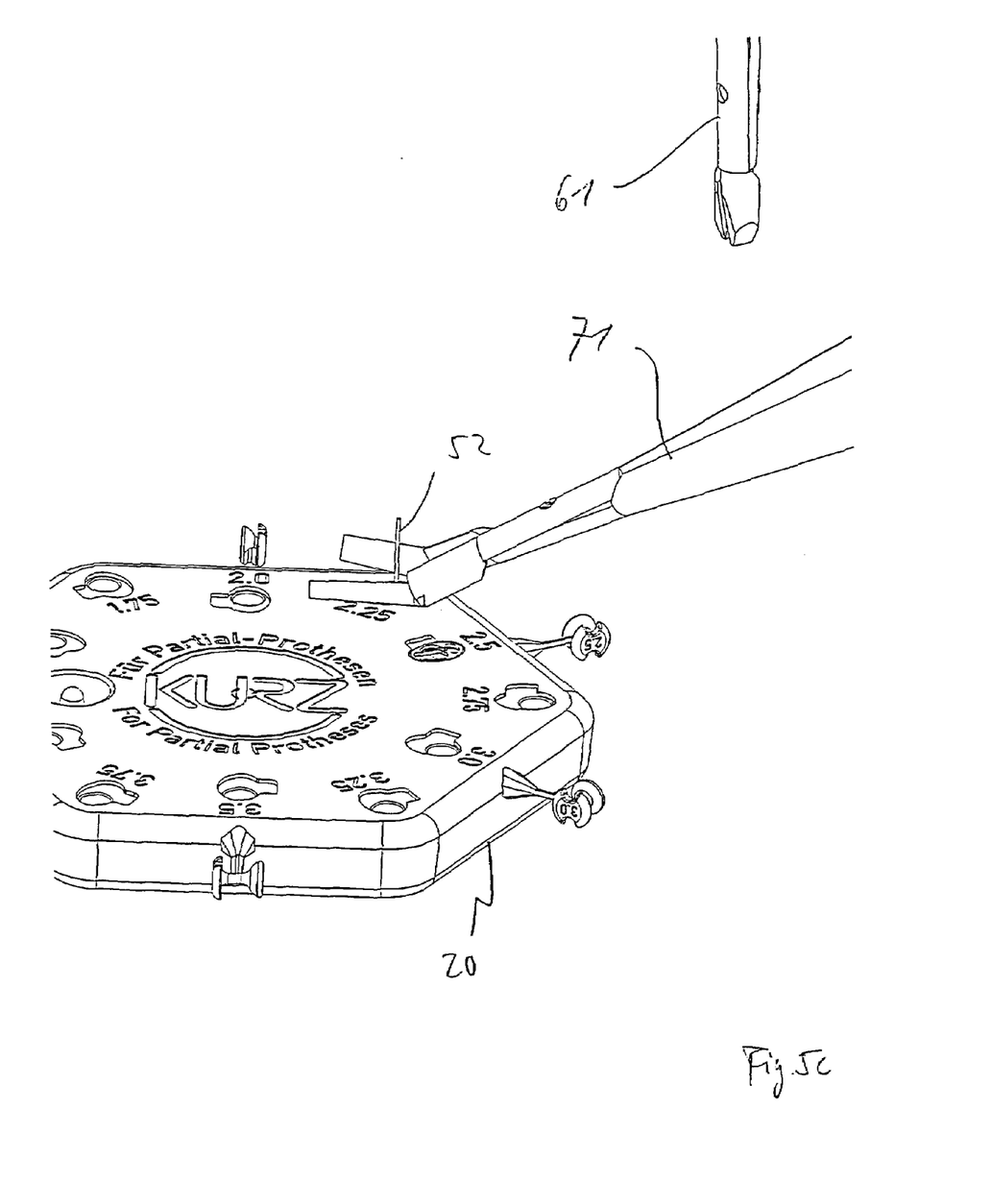
FIG. 5c shows the shaping of a middle ear prosthesis inserted into the recess by means of micro-nippers.

FIG. 5c depicts another work step in the machining of a partial prosthesis for the middle ear: the part of the shaft 52 protruding upward is nipped off using micro-nippers 71.

Figure 5D:
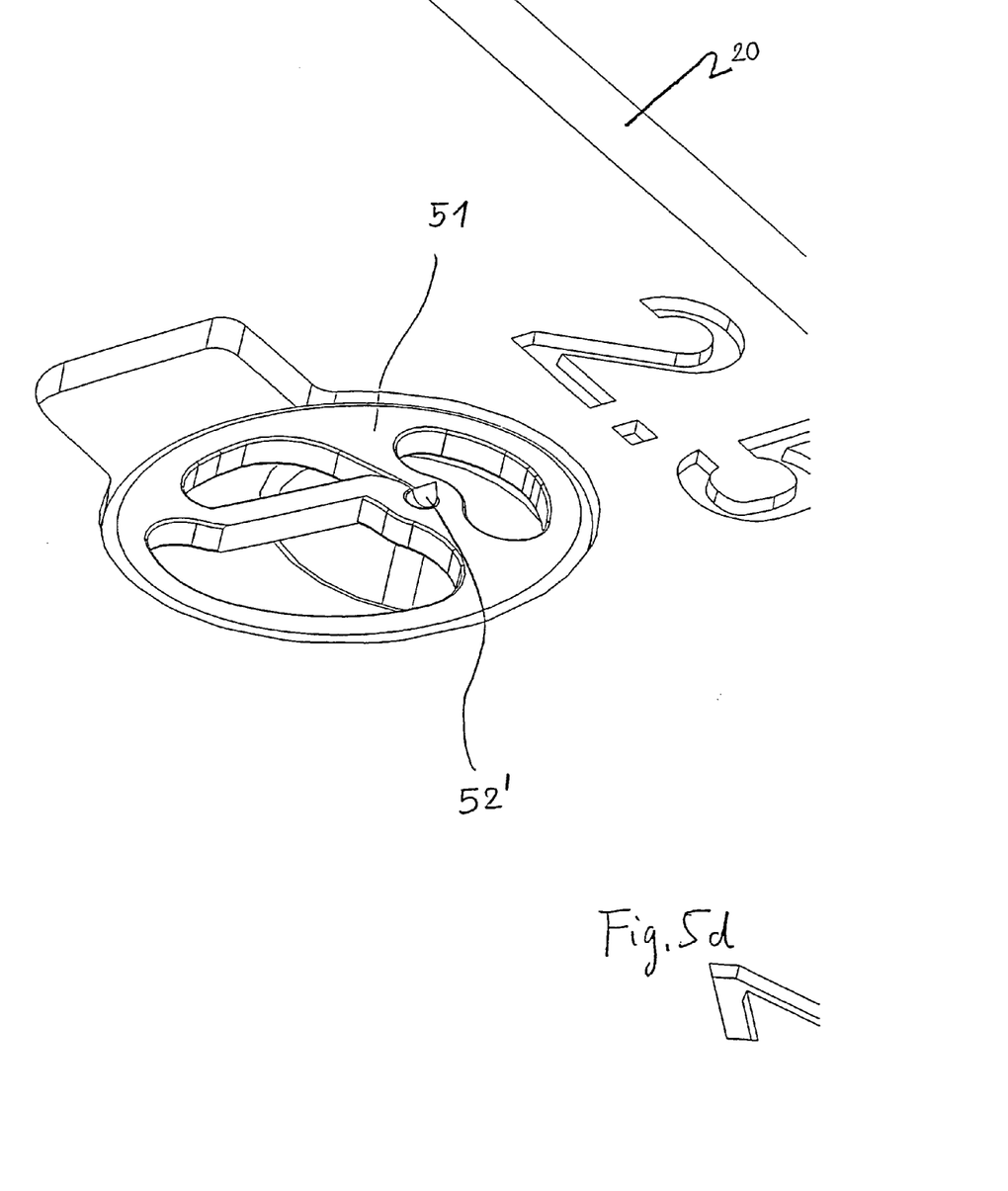
FIG. 5d shows a middle ear prosthesis that has been shaped according to FIG. 5c, after the protruding shaft has been cut off.

Finally, FIG. 5d shows the situation after this work step in which a small, sharp nub 52' of the shaft 52 is visible, which serves as a fixing pin for the cartilage or fascia plate that will subsequently rest against it.

Figure 6A:
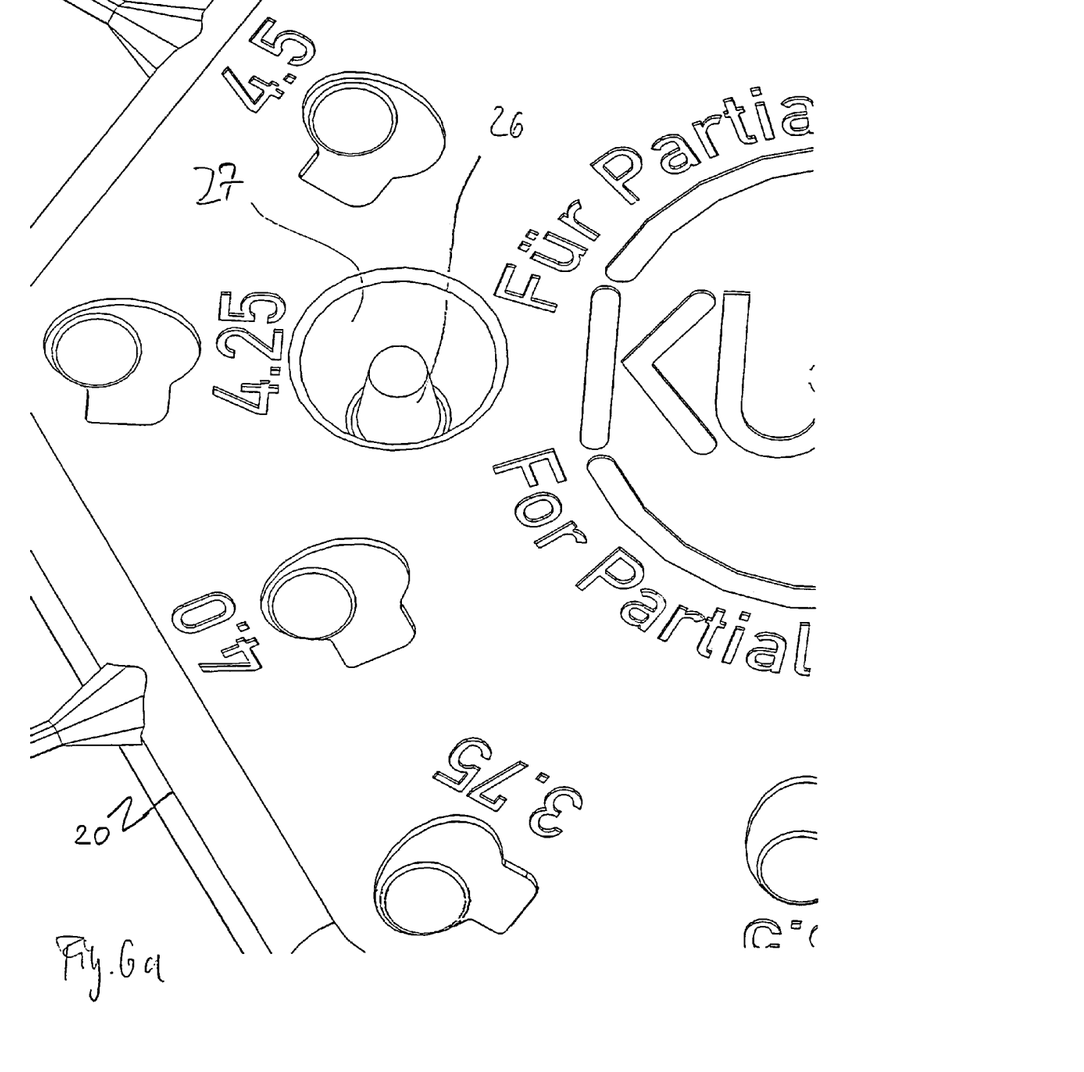
FIG. 6a shows a detail of an embodiment form with a conical protrusion for shaping the bell of a partial prosthesis for the middle ear.
Figure 6B:
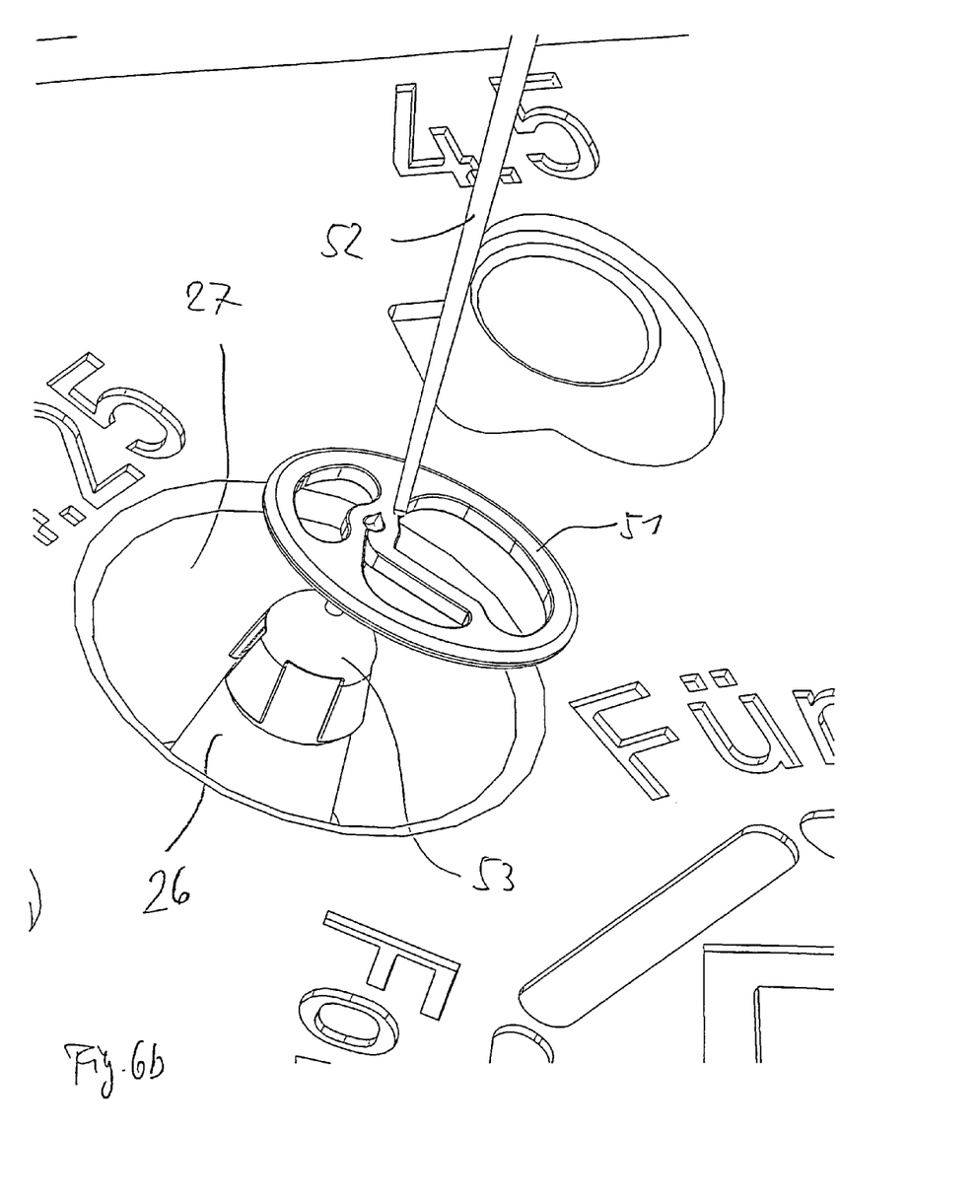
FIG. 6b shows an enlarged detail from FIG. 6a, with a bell of a partial prosthesis for the middle ear being placed onto the tip of the cone.

FIG. 6a is an enlarged view of the conical protrusion from the embodiment form according to FIG. 2. FIG. 6b shows an even greater enlargement of the work step for widening the inner diameter of a bell 63 provided under the head plate 51 of a partial prosthesis for the middle ear. The bell 53 serves for subsequent attachment of the middle ear prosthesis to the stapes of the middle ear.

Figure 7:
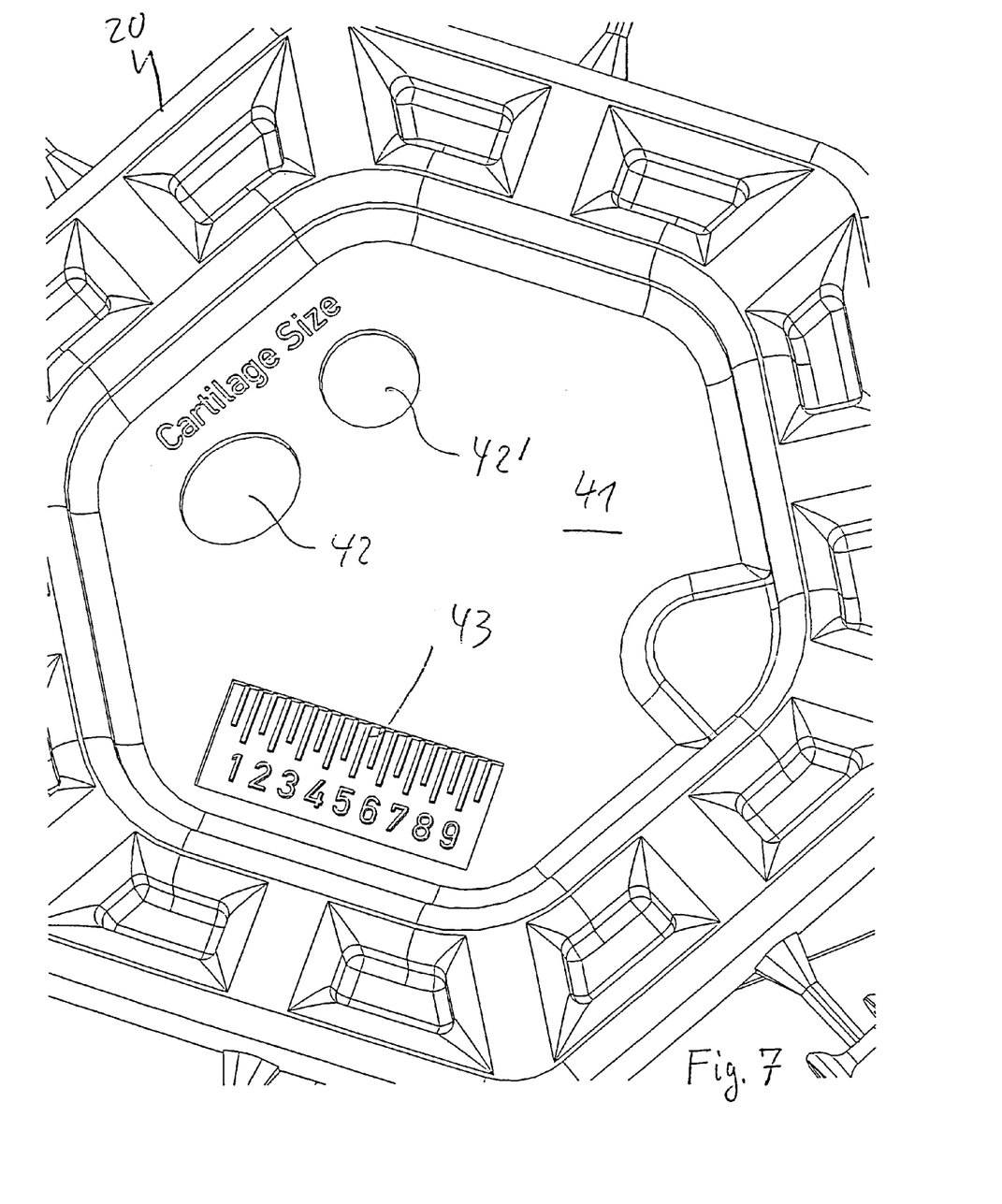
FIG. 7 is an enlarged depiction of the preparation area of an embodiment form similar to the one in FIG. 4.

Finally, FIG. 7 once again shows the flat preparation area 41 with the hollows 42, 42' for accommodating cartilage or fascia disks as well as a graduated length scale 43.

What is claimed is:

1. A device for determining a required length of a middle ear prosthesis, comprising a disk-shaped base part to which prosthesis mockups or prostheses of different lengths are fastenable, which, after being detached from said base part, are insertable by an applicator into a middle ear of a patient during an operation for length determination purposes, said base part being provided with accessories for a step selected from the group consisting of measuring, shaping, and both of the middle ear prosthesis to be inserted, said accessories including at least one recess provided on a side selected from the group consisting of a top side, a bottom side, and both of said disk-shaped base part, which has an inner diameter that corresponds to an outer diameter of a head plate of the middle ear prosthesis to be inserted.

2. A device as defined in claim 1, wherein said base part, under each said recess, has a cavity extending into said base part.

3. A device as defined in claim 2, wherein said recess is configured to accommodate a bell, which is mounted under the head plate of the middle ear prosthesis and used to attach the middle ear prosthesis to stapes of the middle ear.

4. A device as defined in claim 2, wherein said recess is configured to accommodate a strut, which is mounted under the head plate of the middle ear prosthesis and used to support a middle ear prosthesis on a stapedial foot plate of the middle ear.

5. A device as defined in claim 2, wherein said recess has an inner diameter with a contour partially corresponding to an outer contour of the head plate of the middle ear prosthesis, but in at least one section is widened radially outwardly in comparison to a maximum outer diameter of the head plate.

6. A device as defined in claim 1, wherein said base part is provided with a number of recesses, which correspond to outer diameters of head plates of middle ear prostheses and are of different depths.

7. A device as defined in claim 6, wherein said recesses are distributed over a circumference of said base part.

8. A device as defined in claim 6, wherein said base part is provided with an element selected from the group consisting of a mark and a label and arranged next to each of said recesses, which correlates to a dimension selected from the group consisting of a respective depth of a corresponding one of said recesses and a length of the head plate accomodatable therein, a size of an inner diameter of a corresponding one of said recesses and an outer diameter of the head plate, a shape of said recess and the head plate, and combinations thereof.

9. A device as defined in claim 1, wherein said accessories include at least one conical protrusion configured for widening an inner diameter of a bell, which is mounted under the head plate of the middle ear prosthesis and used to attach the inner ear prosthesis to stapes of the middle ear.

10. A device as defined in claim 9, wherein said at least one conical protrusion has a rounded tip that protrudes from one side of said base part and situated in a hollow.

11. A device as defined in claim 9, wherein said conical protrusion is situated on a same side of said disk-shaped base part as said recess for accommodating the head plate of a middle ear prosthesis.

12. A device as defined in claim 1, wherein said accessories include at least one hollow configured for accommodating a cartilage or fascia disk that serves as an insert between the middle ear prosthesis and an ear drum in order to mechanically protect the latter.

13. A device as defined in claim 12, wherein said hollow is configured for providing a step selected from the group consisting of measuring, shaping, and both of the cartilage or facia disk.

14. A device as defined in claim 12, wherein said hollow for accommodating cartilage or facia disks has a contour selected from the group consisting of a round contour and an oval contour.

15. A device as defined in claim 1, wherein said base part is provided with a number of hollows having different dimensions selected from the group consisting of different size inner diameters, different depths, and both.

16. A device as defined in claim 1, wherein said accessories include at least one essentially flat preparation area on at least one side of said disk-shaped base part.

17. A device as defined in claim 16; and further comprising a length scale provided on a surface of said base part at least at one location of said preparation area.

18. A device as defined in claim 17, wherein said scale is calibrated in millimeters.

19. A device as defined in claim 12, wherein said accessories include at least one substantially flat preparation area on at least one side of said disk-shaped base part, said at least one hollow for accommodating cartilage of facia disk being situated in said preparation area.

20. A device as defined in claim 12, wherein said recesses for accommodating the head plate of a middle ear prosthesis and a preparation area provided in said accessories are situated on two different sides of said disk-shaped base part.

21. A device as defined in claim 12, wherein said recesses for accommodating the head plate of the middle ear prosthesis, a preparation area provided in the accessories, and at least one hollow for accommodating cartilage or facia disks are situated on two different sides of said disk-shaped base.

22. A device as defined in claim 20, wherein said recesses and said preparation area are located on the two different sides which are opposing sides.

23. A device as defined in claim 1; and further comprising bridged pieces arranged so that the prosthesis mockups are attached to said bridge pieces and distributed like satellites around an outer circumference of said disk-shaped base part.

24. A device as defined in claim 1; and further comprising a plurality of protective projections situated between each pair of prosthesis mockups and distributed over a circumference of said disk-shaped base part so as to protrude beyond the prosthesis mockups in a radial direction.

25. A device as defined in claim 24, wherein said protective projections are configured as rod-shaped projections.

26. A device as defined in claim 24, wherein said disk-shaped base part has a polygonal outer circumference, said protective projections protruding outwards in the radial direction from vertices of said base part.

27. A device as defined in claim 26, wherein the outer circumference of said disk-shaped base part has the polygonal shape selected from the group consisting of a hexagonal shape and an orthogonal shape.

28. A device as defined in claim 1, wherein said prosthesis mockups are of different sizes.

29. A device as defined in claim 28, wherein said prosthesis mockups have different lengths.

30. A device as defined in claim 1, wherein said recesses are configured to correspond to outer diameters of the head plates of the middle ear prosthesis and are of different respective depth, the prosthesis mockups being situated on an outer circumference of said base part, each in a radial vicinity of a respective one of said recesses for accommodating the head plate of the middle ear prosthesis, said recess having a size which corresponds to a size of the prosthesis mockups respectively adjacent to it.

31. A device as defined in claim 30, wherein said recesses are distributed over a circumference of said base part.

32. A device as defined in claim 23, wherein said base part, said bridge pieces, and the prosthesis mockups are formed as injection molded plastic parts.

33. A device as defined in claim 32, wherein said base part, said bridge pieces and the prosthesis mockups are integrally joined to one another.

34. A device for determining a required length of a middle ear prosthesis, comprising a disk-shaped base part to which prosthesis mockups or prostheses of different lengths are fastenable, after being detached from said base part, are insertable by an applicator into a middle ear of a patient during an operation for length determining purposes, said base part being provided with accessories for a step selected from the group consisting of measuring, shaping, and both of the middle ear prosthesis to be inserted, said accessories including at least one conical protrusion that protrudes from one side of said base part and used to widen an inner diameter of a bell which is mounted under a head plate of the middle ear prosthesis and used to attach the middle ear prosthesis to stapes of the middle ear.

35. A device as defined in claim 34, wherein said at least one conical protrusion has a rounded tip that protrudes from one side of said base part and situated in a hollow.

36. A device for determining a required length of a middle ear prosthesis, comprising a disk-shaped base part to which prosthesis mockups or prostheses of different lengths are fastenable, which after being detached from said base part are insertable by an applicator into a middle ear of a patient during an operation for length determination purposes, said base part being provided with accessories for a step selected from the group consisting of measuring, shaping and both of the middle ear prosthesis to be inserted, said accessories including at least one hollow in said base part, which is configured for accommodating a cartilage or facia disk that serves as an insert between the middle ear prosthesis and an eardrum in order to mechanically protect the latter.

37. A device as defined in claim 36, wherein said accessories include several hollows in said base part, which are configured for accommodating a cartilage or facia disk.

38. A device as defined in claim 36, wherein said at least one hollow is configured also for performing a step selected from the group consisting of measuring, shaping, and both of a cartilage of facia disk.

* * * * *